United States Patent
Nakano et al.

(10) Patent No.: US 10,569,023 B2
(45) Date of Patent: Feb. 25, 2020

(54) MEDICAL SYRINGE, GASKET USED FOR SYRINGE AND METHOD FOR PRODUCING SAME

(71) Applicant: SUMITOMO RUBBER INDUSTRIES, LTD., Kobe-shi, Hyogo (JP)

(72) Inventors: Hiroaki Nakano, Kobe (JP); Seiji Hara, Kobe (JP); Hiroyuki Kaneko, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 940 days.

(21) Appl. No.: 15/038,539

(22) PCT Filed: Jan. 22, 2015

(86) PCT No.: PCT/JP2015/051707
§ 371 (c)(1),
(2) Date: May 23, 2016

(87) PCT Pub. No.: WO2015/118958
PCT Pub. Date: Aug. 13, 2015

(65) Prior Publication Data
US 2016/0287800 A1    Oct. 6, 2016

(30) Foreign Application Priority Data

Feb. 5, 2014    (JP) .................................. 2014-020762

(51) Int. Cl.
*A61M 5/315*    (2006.01)
*B29B 13/08*    (2006.01)
(Continued)

(52) U.S. Cl.
CPC ......... *A61M 5/31513* (2013.01); *B29B 13/08* (2013.01); *B29C 35/002* (2013.01);
(Continued)

(58) Field of Classification Search
CPC ............ A61M 5/31513; A61M 5/3129; A61M 2005/3132; B29C 35/02
See application file for complete search history.

(56) References Cited

U.S. PATENT DOCUMENTS 4,997,423 A *    3/1991    Okuda ................ A61M 5/2429
                                                                                 604/218
6,090,081 A      7/2000    Sudo et al.
(Continued)

FOREIGN PATENT DOCUMENTS

EP    0 375 778 A1    7/1990
EP    2781231 A2 *    9/2014    ........... A61L 31/084
(Continued)

OTHER PUBLICATIONS

Extended European Search Report dated Jul. 24, 2017, for European Application No. 15746538.6.

*Primary Examiner* — Emily L Schmidt
*Assistant Examiner* — Tiffany Legette
(74) *Attorney, Agent, or Firm* — Birch, Stewart, Kolasch & Birch, LLP

(57) ABSTRACT

In a conventional laminated gasket production method, when a product of a laminated gasket is demolded from a mold, the product is rubbed against the mold and, therefore, minute scratches are formed on a surface of the laminated gasket. These minute scratches are liable to prevent reliable sealing of a liquid drug. The present invention is a method for producing a gasket to be used for a medical syringe and is characterized by including the steps of: preparing a gasket molding mold; molding a gasket having a circumferential
(Continued)

surface portion in the mold with the gasket being laminated with a lamination film; and demolding the gasket from the mold, and then forming a groove only in the lamination film circumferentially of the circumferential surface portion of the gasket.

19 Claims, 2 Drawing Sheets

(51) Int. Cl.
- *B29C 35/00* (2006.01)
- *B29C 35/02* (2006.01)
- *B29C 59/00* (2006.01)
- *B29C 59/02* (2006.01)
- *B29C 59/16* (2006.01)
- *B29L 31/00* (2006.01)
- *B29C 45/14* (2006.01)
- *B29K 105/24* (2006.01)
- *B29L 31/26* (2006.01)

(52) U.S. Cl.
CPC ............ *B29C 35/02* (2013.01); *B29C 59/007* (2013.01); *B29C 59/02* (2013.01); *B29C 59/16* (2013.01); *A61M 2207/00* (2013.01); *B29C 45/14* (2013.01); *B29K 2105/24* (2013.01); *B29L 2031/265* (2013.01); *B29L 2031/7544* (2013.01)

(56) References Cited

U.S. PATENT DOCUMENTS

| | | |
|---|---|---|
| 2005/0137533 A1 | 6/2005 | Sudo et al. |
| 2006/0178643 A1 | 8/2006 | Sudo et al. |
| 2013/0040156 A1 | 2/2013 | Nakano et al. |
| 2014/0288508 A1* | 9/2014 | Iwano ............... A61L 31/084 604/222 |
| 2014/0319778 A1 | 10/2014 | Kawasaki et al. |
| 2014/0339777 A1 | 11/2014 | Nakano et al. |
| 2015/0344803 A1 | 12/2015 | Minagawa |

FOREIGN PATENT DOCUMENTS

| | | |
|---|---|---|
| JP | 64-085665 A | 3/1989 |
| JP | 7-025953 Y2 | 6/1995 |
| JP | 3282322 B2 | 5/2002 |
| JP | 2003-190285 A | 7/2003 |
| JP | 2004-162761 A | 6/2004 |
| JP | 2005-160888 A | 6/2005 |
| JP | 4908617 B2 | 4/2012 |
| JP | 2013-138697 A | 7/2013 |
| JP | 2013-192634 A | 9/2013 |
| JP | 2014-131856 A | 7/2014 |
| JP | 2014-180511 A | 9/2014 |
| JP | 2014-213092 A | 11/2014 |
| JP | 2014-223149 A | 12/2014 |

\* cited by examiner

MEDICAL SYRINGE, GASKET USED FOR SYRINGE AND METHOD FOR PRODUCING SAME

TECHNICAL FIELD

The present invention relates to a medical syringe, particularly to a gasket to be used for the medical syringe, and a gasket production method.

BACKGROUND ART

Syringes prefilled with a liquid drug (generally referred to as "prefilled syringes") are used as medical syringes. The prefilled syringes are advantageous because of their handling ease without the need for transferring the liquid drug into the syringe. Further, transfer of a wrong liquid drug into the syringe is advantageously prevented. Therefore, the prefilled syringes are increasingly used in recent years.

Unlike conventional syringes into which a liquid drug sucked up from a vial or other container is transferred immediately before use, the prefilled syringes are each required to serve as a container which is kept in contact with the liquid drug for a long period of time.

Such a syringe typically includes a syringe body, a plunger reciprocally movable in the syringe body, and a gasket attached to a distal end of the plunger.

The gasket to be used for the syringe is generally made of a crosslinked rubber. It is known that the crosslinked rubber contains various crosslinking components, and these crosslinking components and their thermally decomposed products are liable to migrate into the liquid drug when the liquid rug is kept in contact with the syringe. It is also known that these migrating components adversely influence the efficacy and the stability of some liquid drug.

The gasket is required to be smoothly slidable when the syringe is used. In general, the gasket made of the crosslinked rubber is poorer in slidability. To cope with this, it is a general practice to apply silicone oil to an inner surface of the syringe body. However, it is known that the silicone oil adversely influence the efficacy and the stability of some liquid drug.

From this viewpoint, a product of so-called "laminated gasket" including a rubber gasket body having a surface laminated with a film having excellent slidability is often used for the medical syringe. Since the surface of the rubber gasket body of the laminated gasket is covered with the highly slidable film, it is possible to prevent the components of the crosslinked rubber from migrating into the liquid drug, and to ensure the slidability even without the use of the silicone oil.

CITATION LIST

Patent Document

Patent Document 2: JP-HEI7 (1995)-25953-U

SUMMARY OF THE INVENTION

Problem to be Solved by the Invention

In the laminated gasket, however, the film to be used for laminating the surface is not elastic and, therefore, is liable to impair the elasticity of the inside crosslinked rubber. The elasticity of the overall gasket is an essential requirement for reliable sealing of the liquid drug contained in the syringe body. If the gasket has insufficient elasticity, the liquid drug contained in the syringe body is liable to leak out of the syringe.

The inventor conducted studies to solve this problem. As a result, the inventor found that a laminated gasket free from the leakage of the liquid drug can be provided by controlling the thickness of the film to be used for the lamination and modifying the surface of the film.

In a rubber product production process, a rubber is generally vulcanization-molded in a mold having a cavity defining a desired product shape and, after the rubber is shaped, the resulting product is demolded from the mold. In the conventional production process, when the product of the laminated gasket is demolded from the mold, the product is rubbed against the mold and, therefore, minute scratches are formed on the surface of the laminated gasket. These minute scratches are liable to prevent the reliable sealing of the liquid drug. Since the surface is laminated with the film layer during the molding of the laminated gasket, the fillability (conformability and transformability) of the cavity of the mold is poorer. It was also found that, even if the mold is formed with a minute groove structure or the like, perfect transfer of the structure to the film layer is difficult.

Thus, the inventor invented a production method for a novel laminated gasket which could not be produced by the conventional production method.

Solution to Problem

A laminated gasket to be used for a medical syringe according to the present invention, a medical syringe according to the present invention, and a laminated gasket production method according to the present invention are specified in the claims.

Specific description is as follows:

According to a first inventive aspect of the present invention, there is provided a gasket to be used for a medical syringe, the gasket including a main body made of an elastic material, and a lamination film provided on a surface of the main body, the gasket having a circumferential surface portion to be brought into contact with an inner peripheral surface of a syringe body of the syringe, and having a groove formed circumferentially in a portion of the lamination film present in the circumferential surface portion thereof, wherein the groove is present only in a surface of the lamination film.

According to a second inventive aspect of the present invention, the lamination film has a smaller thickness in the portion thereof formed with the groove than in the other portion thereof not formed with the groove in the gasket of the first aspect of the present invention.

According to a third inventive aspect of the present invention, the groove has a depth of not less than 1 μm and not greater than 50 μm in the gasket of the first and second aspects of the present invention.

According to a fourth inventive aspect of the present invention, the depth of the groove is not less than 5 μm and not greater than 15 μm in the gasket of the third aspect of the present invention.

According to a fifth inventive aspect of the present invention, the groove has a width of not less than 1 μm and not greater than 100 μm in the gasket of the first and second aspects of the present invention.

According to a sixth inventive aspect of the present invention, the groove includes at least one annular groove extending circumferentially of the circumferential surface portion in the gasket of the first aspect of the present invention.

According to a seventh inventive aspect of the present invention, the lamination film has a thickness of not less than 20 μm and not greater than 50 μm in the gasket of the first aspect of the present invention.

According to an eighth inventive aspect of the present invention, there is provided a medical syringe, which includes a tubular syringe body, a plunger combined with the syringe body and reciprocally movable in the syringe body, and a gasket of anyone of the first through seventh aspects of the present invention attached to a distal end of the plunger.

According to a ninth inventive aspect of the present invention, the medical syringe of the eighth aspect of the present invention is a prefilled syringe in which the syringe body is prefilled with a liquid drug.

According to a tenth inventive aspect of the present invention, there is provided a method for producing a gasket to be used for a medical syringe, the method including the steps of: preparing a gasket molding mold; molding a gasket having a circumferential surface portion in the mold with the gasket being laminated with a lamination film; and demolding the gasket from the mold, and then forming a groove only in the lamination film circumferentially of the circumferential surface portion of the gasket.

According to an eleventh inventive aspect of the present invention, the gasket molding step includes the step of placing an unvulcanized rubber in superposition on an inner surface of the lamination film in the mold, and vulcanization-molding the rubber in the gasket production method of the tenth aspect of the present invention.

According to a twelfth inventive aspect of the present invention, the gasket molding step includes the step of roughening the inner surface of the lamination film before superposing the rubber on the inner surface of the lamination film in the gasket production method of the eleventh aspect of the present invention.

According to a thirteenth inventive aspect of the present invention, the groove forming step includes the step of cutting a surface of the lamination film in the gasket production method of the tenth aspect of the present invention.

According to a fourteenth inventive aspect of the present invention, the groove forming step includes the step of laser-processing the lamination film in the gasket production method of the thirteenth aspect of the present invention.

Effects of the Invention

According to the present invention, the laminated gasket for the medical syringe can be provided, which is excellent in sealability. The laminated gasket is particularly advantageous for a prefilled syringe.

According to the present invention, the medical syringe, particularly the prefilled syringe, can be provided, which is excellent in sealability, and free from adverse influence on the efficacy and the stability of a liquid drug even if the syringe is kept in contact with the liquid drug for a long period of time.

In the present invention, deformation of the groove can be suppressed if the width of the groove formed only in the surface of the lamination film is not greater than 100 μm. This more advantageously prevents the liquid leakage. If the depth of the groove is not less than 1 μm, the liquid leakage can be more advantageously prevented.

According to the present invention, the laminated gasket production method can be provided for producing a laminated gasket having excellent sealability.

EMBODIMENT OF THE INVENTION

With reference to the attached drawings, one embodiment of the present invention will hereinafter be described specifically.

Figure 1:
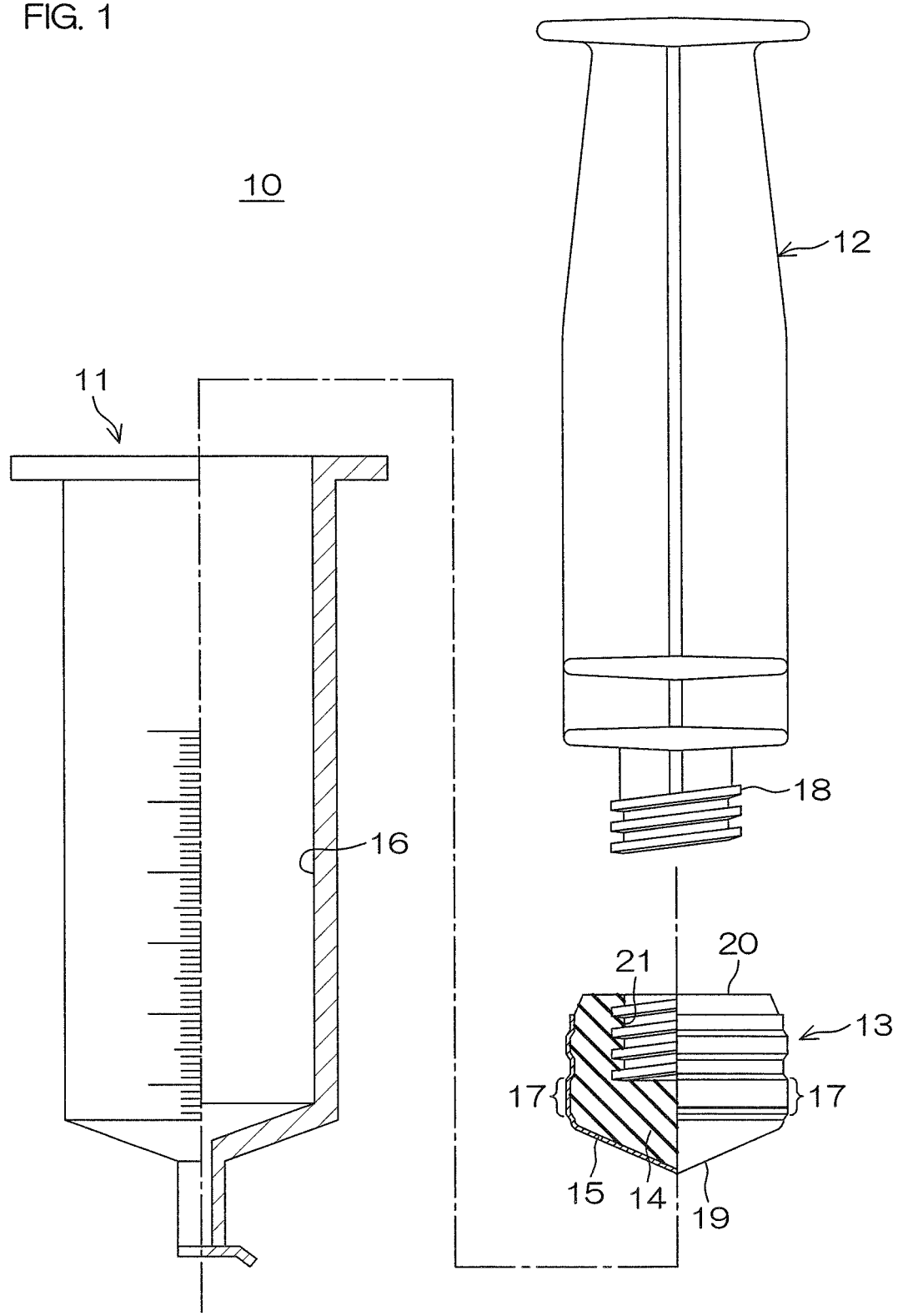
FIG. 1 is an exploded diagram illustrating a medical syringe according to an embodiment of the present invention.

FIG. 1 is an exploded diagram illustrating a medical syringe, i.e., a so-called prefilled syringe, according to the embodiment of the present invention. In FIG. 1, a half of a syringe body 11 and a half of a gasket 13 are illustrated in section.

Referring to FIG. 1, the prefilled syringe 10 includes a hollow cylindrical syringe body 11, a plunger 12 combined with the syringe body 11 and reciprocally movable in the syringe body 11, and a gasket 13 attached to a distal end of the plunger 12. The gasket 13 is a so-called laminated gasket, which includes a main body 14 made of an elastic material (a rubber or an elastomer) and a lamination film 15 provided on a surface of the main body 14. The gasket 13 includes a circumferential surface portion 17 to be kept in gas-tight and liquid-tight contact with an inner peripheral surface 16 of the syringe body 11.

The plunger 12 includes a resin plate piece, for example, having a cross shape as seen in section, and a head 18 provided at a distal end of the resin plate piece and fitted with the gasket 13. The head 18 is an integral part of the plunger 12 made of a resin and shaped in a male screw.

The gasket 13 has a generally cylindrical shape having a short axis. The gasket 13 has a distal end face, for example, having a conical center portion projecting at an obtuse angle, and a rear end face axially recessed into an engagement recess 21 shaped in a female screw. The head 18 of the plunger 12 is screwed into the engagement recess 21 of the gasket 13, whereby the gasket 13 is attached to the distal end of the plunger 12.

Figure 2:
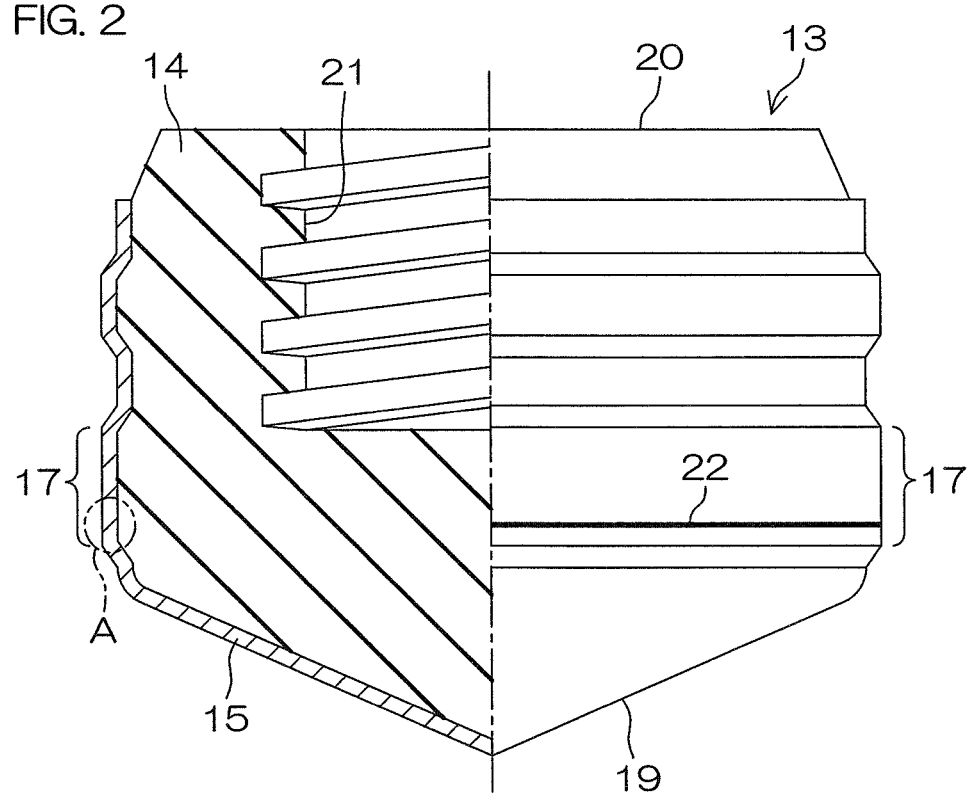
FIG. 2 is a diagram of a laminated gasket according to the embodiment of the present invention with a half of the gasket illustrated in section.

FIG. 2 is a diagram showing only the gasket 13 of FIG. 1 on an enlarged scale. In FIG. 2, a half of the gasket 13 is illustrated in section.

Referring to FIG. 2, the structure of the gasket 13 according to this embodiment will be described in greater detail.

The gasket 13 includes the main body 14, and the lamination film 15 provided on the surface of the main body 14. The main body 14 is merely required to be made of an elastic material, which is not particularly limited. Examples of the elastic material include thermosetting rubbers and thermoplastic elastomers. Particularly, the thermosetting rubbers and dynamically crosslinkable thermoplastic elastomers having crosslinking sites are more preferred because they are heat-resistant. The polymer component is not particularly limited, but preferred examples of the polymer component include ethylene-propylene-diene rubbers and butadiene rubbers which are excellent in moldability. Other preferred examples of the polymer component include butyl rubbers, chlorinated butyl rubbers and brominated butyl rubbers which are excellent in gas permeation resistant.

The type of the lamination film 15 to be provided on the surface of the main body 14 is not particularly limited, as long as the lamination film is capable of preventing migration of substances from the crosslinked rubber (main body 14) and has more excellent slidability, i.e., a smaller friction coefficient, than the rubber. Examples of the lamination film include films of very high molecular weight polyethylenes and fluororesins which are proved to be practical in medical applications. Particularly, the fluororesins are preferred because they are excellent in slidability and have chemically stable surfaces. Usable examples of the fluororesins include conventionally known fluorine-containing resins, such as PTFE, modified PTFE, ethylene tetrafluoroethylene copolymers (ETFE) and perfluoroalkyl ether (PFA). The PTFE and the modified PTFE are preferred because of their slidability and chemical stability. The ETFE is preferred because of its resistance to γ-ray to be used for sterilization. For adhesiveness to the main body 14, a film made of a mixture of these resins or a laminate film may be used.

Features of the laminated gasket 13 according to this embodiment are that the gasket 13 includes the circumferential surface portion 17 to be kept in gas-tight and liquid-tight contact with the inner peripheral surface 16 of the syringe body 11, and that a groove 22 is formed only in the surface of the lamination film 15 circumferentially of the circumferential surface portion 17 of the gasket 13.

The groove 22 is an annular groove extending circumferentially of the circumferential surface portion 17. In this embodiment, a single groove 22 is provided by way of example.

It is merely necessary to provide at least one groove 22, and a plurality of grooves may be provided so as to be axially spaced a predetermined distance from each other. There is no need to define an upper limit in the number of the grooves. The groove 22 is not necessarily required to be an annular groove extending continuously circumferentially, but may be discontinuous. At least one groove is preferably present along the entire circumference of the circumferential surface portion 17.

The groove 22 is preferably an annular groove extending circumferentially of the circumferential surface portion 17 from a starting point to an end point located at the same position as the starting point. This provides a liquid drug sealing effect to uniformly seal the liquid drug circumferentially of the circumferential surface portion 17. With the circumferential surface portion 17 of the gasket 13 being seen in a development elevation, the groove 22 preferably extends generally linearly.

Figure 3:
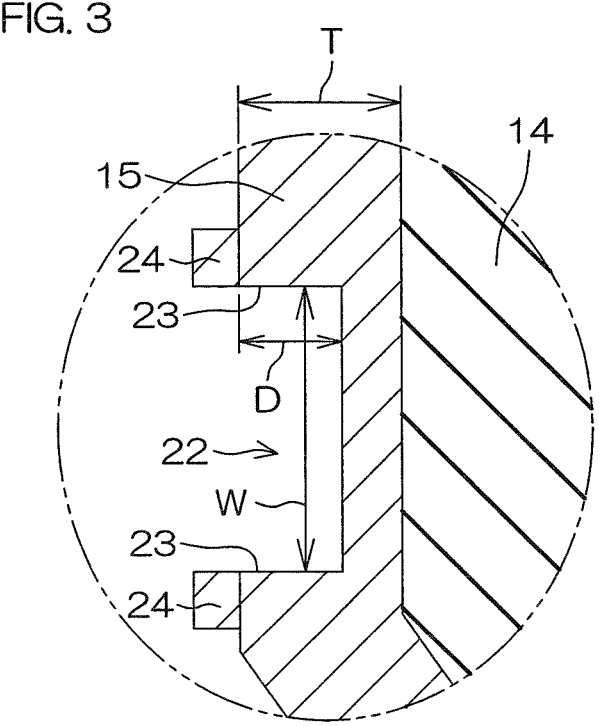
FIG. 3 is an enlarged sectional view of a portion A in FIG. 2.

FIG. 3 is an enlarged partial sectional view of the single groove 22 formed in the circumferential surface portion 17 of FIG. 2, i.e., an enlarged sectional view of a portion A in FIG. 2. Referring to FIG. 3, the groove 22 is recessed from the surface of the lamination film 15, but the main body 14 is not recessed in conformity with the groove 22. That is, the groove 22 never influences the shape of the main body 14, but is formed only in the lamination film 15. This is one of the features of this embodiment.

Therefore, the thickness of a portion of the lamination film 15 formed with the groove 22 is smaller than the thickness T of the other portion of the lamination film 15 not formed with the groove 22.

The groove 22 has a depth D of, for example, not less than 1 μm and not greater than 50 μm, preferably not less than 5 μm and not greater than 15 μm.

A groove depth of not less than 5 μm is preferred for easy and uniform formation of the groove.

The sectional shape of the groove to be formed is not particularly limited. For productivity, the groove preferably has a simply recessed sectional shape or a rounded recessed sectional shape.

The groove 22 preferably has a width W of not greater than 100 μm, desirably not greater than 50 μm. A groove width W of 1 μm or less is not preferred because an intended effect cannot be created.

Projections 24 each having a thickness slightly greater than the original thickness T of the lamination film 15 may be provided along outer edges 23 of the groove 22.

Where the formation of the groove 22 is achieved, for example, by cutting the surface of the lamination film 15 by means of a cutting blade, a part of the material (a surface portion of the lamination film 15) is compressed to form burrs along the outer edges 23 of the groove 22 by a stress. Thus, the projections 24 are formed. Where the formation of the groove 22 is achieved by laser beam processing, a surface portion of the lamination film 15 is evaporated or decomposed by laser beam, and a part of the material is re-deposited along the outer edges 23 of the groove 22 to form the projections 24.

The laminated gasket 13 is molded by means of the mold, and then demolded from the mold. At this time, the laminated gasket 13 is rubbed against the mold and, therefore, minute scratches are formed on the surface of the laminated gasket 13. However, the minute scratches are repaired by the projections 24 when the groove 22 is formed in the demolded laminated gasket 13. Therefore, the presence of the projections 24 along the outer edges of the groove 22 is rather preferred.

The thickness T of the lamination film 15 is preferably smaller. In practical applications, a lamination film having a thickness of about 20 μm to about 50 μm is generally used. In this embodiment, therefore, a lamination film having a thickness T falling within this range is used as the lamination film 15.

Next, a method for producing the gasket 13 according to this embodiment will be described.

The gasket 13 according to this embodiment is produced through the following production process steps:
(1) Preparing a gasket molding mold;
(2) Molding a gasket laminated with a lamination film in the mold; and
(3) Demolding the laminated gasket from the mold, and then forming a groove only in a surface of the lamination film circumferentially of a circumferential surface portion of the gasket.

In the step of molding the gasket laminated with the lamination film in the mold, an unvulcanized rubber is placed on an inner surface of the lamination film in the mold, and vulcanization-molded.

For example, a sheet of an unvulcanized rubber containing a crosslinking agent is stacked on a lamination film, and vulcanization-molded into a predetermined shape in the mold.

In this case, the inner surface of the lamination film 15 on which the rubber is placed is preferably preliminarily roughened. With the inner surface of the film 15 roughened, the rubber can firmly adhere to the film 15 by the vulcanization molding without the use of an adhesive agent. The adhesion is attributable to an anchoring effect which is created with the vulcanized rubber intruding into voids formed in the roughened inner surface of the film 15.

The modification (roughening) of the inner surface of the lamination film 15 may be achieved, for example, by applying ion beam to the inner surface to break the internal molecular structure in the inner surface (see, for example, JP4908617).

Another production method may be employed which includes the steps of applying an adhesive layer on an inner surface of a lamination film not roughened, superposing an unvulcanized rubber material on the adhesive layer, and putting the lamination film and the rubber material in a mold to mold the gasket in the mold.

After the gasket is molded in the mold, the groove is formed on the gasket. Thus, the gasket is produced as having excellent sealability.

If a production method in which the groove is formed simultaneously with the molding of the gasket is employed, i.e., if a production method in which a groove structure is preliminarily formed in the mold and transferred to the surface of the gasket is employed, the molded gasket would be damaged or minute scratches would be formed on the molded gasket when the gasket is taken out of the mold (demolded).

Even if minute scratches are formed during the demolding of the gasket, the minute scratches are repaired to some extent by forming the groove on the molded gasket in the subsequent groove forming step. Further, the groove formed on the gasket after the molding is advantageous for creating the desired effect.

The following methods may be employed for forming the groove on the gasket after the molding.

Conceivable groove forming processes are as follows:
(1) An external stress is applied to the gasket including the main body laminated with the lamination film for plastic deformation; and
(2) Only a surface portion of the gasket, i.e., only the lamination film, is cut to form the groove.

The latter groove forming process by the cutting is more preferred than the former groove forming process by the plastic deformation because the formation of the groove is easier and the influence of the stress on a portion of the gasket other than a groove formation portion is suppressed.

The cutting process is not particularly limited, but may employ a cutting blade or irradiation with laser beam. The cutting process employing the irradiation with laser beam is more preferred because formation of a minute groove structure is easier and the influence of the stress on a portion of the gasket around the groove formation portion is suppressed.

In the cutting process employing the irradiation with the laser beam, the type and the output dose of the laser beam may be properly determined based on known art. The type of the laser beam may be properly selected according to the film material, the groove depth and the like. A cutting process employing irradiation with infrared laser beam is preferred because of its industrial handling ease. The laser beam irradiation period is properly selected according to the forming conditions. Particularly, short pulse irradiation is preferred because the influence of heat on the portion of the gasket around the groove formation portion is suppressed.

EXAMPLES

Three types of lamination films were each used in combination with an unvulcanized rubber, and gasket structures were produced by vulcanization molding of the rubber. Gaskets (Examples 1 to 8) were each produced by forming an annular groove circumferentially in a circumferential surface portion of each of the gasket structures, and a gasket (Comparative Example 1) was provided without forming an annular groove in the gasket structure.

The following three types of lamination films each having a thickness of 100 μm were used. The lamination films on the circumferential surface portions 17 of the laminated gasket structures each had a thickness of 30 μm.
[Lamination Films Used]
(1) PTFE film (VALFLON (registered trade name) available from Nippon Valqua Industries Ltd.)
(2) Modified PTFE film (VALFLON Ex1 (registered trade name) available from Nippon Valqua Industries Ltd.)
(3) ETFE film (Fluon ETFE (registered trade name) available from Asahi Glass Co., Ltd.)

Inner surfaces of the respective lamination films (on which an unvulcanized rubber sheet was stacked) were each preliminarily irradiated with ion beam to be thereby roughened.
[Main Body Material Used]
Unvulcanized rubber sheet: Halogenated butyl rubber
    Crosslinking agent:
2-di-n-butylamino-4,6-dimercapto-s-triazine  Zisnet  DB (registered trade name) available from Sankyo Kasei Co., Ltd.
[Production Conditions]
Vulcanization temperature: 180° C.
Vulcanization period: 8 minutes
Processing pressure: 20 MPa
[Product Shape]
Gasket shape shown in FIG. 2 with its circumferential surface portion 17 having a diameter of 6.60 mm
[Formation of Groove]
A groove was formed after the product shape was provided. The following two processes were employed for the formation of the groove.
(1) Processing with Laser Beam
Apparatus: Multi-purpose manual laser processor available from Allied Lasers, Inc.
A hybrid laser was used as an oscillator to emit laser beam at a wavelength of 1064 nm. The laser beam had a processing spot diameter of 10 μm. A groove having a desired width was formed by repeatedly applying the laser beam.
(2) Processing with Cutting Blade
A cutting process was performed with the use of a flat face blade (having a width of 100 μm) and a needle blade (having a tip width of 1 μm and a taper angle of 30 degrees). The penetration depth of the blade for the cutting was 2 μm or 0.5 μm.
[Test Method]
Measurement of Dimensions of Groove
By means of a laser microscope (VK-X100 available from Keyence Corporation), the surface geometry of each of the products formed with the grooves was measured with an objective lens having a magnification of 50×. For each of the products, the maximum depth and the width of the groove were measured at four positions on an image of the product, and arithmetic averages were determined for the maximum depth and the width.
Liquid Drug Sealability
The products thus produced were each inserted in a syringe body, which was in turn filled with a test liquid. Then, an opposite end of the syringe body was capped. The resulting syringe body was allowed to stand still at 40° C. for one week, and observed with an objective lens having a magnification of 50× by means of a video microscope (DVM5000 available from Leica Microsystems Inc.) to be checked for liquid leakage. For each product, 20 samples were prepared, and the number of samples suffering from liquid leakage (in which the test liquid penetrated beyond a maximum diameter portion (circumferential surface portion 17) of the gasket) was recorded. A product with two or less samples suffering from the liquid leakage was defined as acceptable. The test liquid herein used was prepared by adding 0.2 g/liter of a colorant (Methylene Blue available from Sigma Aldrich Japan LLC.) and 1.0 g/liter of a surfactant (POLYSORBATE 80 available from NOF Corporation) to water. The syringe body was made of a cycloolefin resin and had an inner diameter of 6.35 mm.

TABLE 1

|  | Example 1 | Example 2 | Example 3 | Example 4 | Example 5 | Example 6 | Example 7 | Example 8 | Comparative Example 1 |
|---|---|---|---|---|---|---|---|---|---|
| Type of film | PTFE | PTFE | PTFE | PTFE | PTFE | PTFE | Modified PTFE | ETFE | PTFE |
| Processing method | Laser | Laser | Laser | Laser | Cutting blade | Cutting blade | Laser | Laser | — |
| Depth (μm) of groove | 8.2 | 8.4 | 13.5 | 34.0 | 1.6 | 1.5 | 8.3 | 10.2 | — |
| Width (μm) of groove | 5.2 | 5.4 | 10.8 | 97.0 | 97.5 | 1.8 | 5.5 | 12.5 | — |
| Number of grooves | 1 | 3 | 3 | 3 | 2 | 2 | 3 | 3 | — |
| Number of samples suffering from liquid leakage | 0 | 0 | 0 | 1 | 1 | 1 | 0 | 0 | 13 |
| Evaluation | *1 | *1 | *1 | *1 | *1 | *1 | *1 | *1 | *2 |

*1: Acceptable
*2: Unacceptable

[Test Results]

The gaskets of Examples 1 to 8 were each excellent with a smaller number of samples suffering from the liquid leakage as compared with the gasket of Comparative Example 1 not formed with the groove after the molding.

REFERENCE SIGNS LIST

10: PREFILLED SYRINGE
11: SYRINGE BODY
12: PLUNGER
13: GASKET
14: MAIN BODY
15: LAMINATION FILM
17: CIRCUMFERENTIAL SURFACE PORTION
22: GROOVE

The invention claimed is:

1. A gasket to be used for a medical syringe, the gasket comprising:
a main body made of an elastic material; and
a lamination film provided on a surface of the main body,
wherein the gasket has a circumferential surface portion to be kept in gas-tight and liquid-tight contact with an inner peripheral surface of a syringe body of the syringe,
wherein the circumferential surface portion includes a circumferential main body portion made of the elastic material and a circumferential lamination film portion provided on a surface of the circumferential main body portion,
wherein the circumferential lamination film portion has a groove,
wherein the groove is formed only in a surface of the circumferential lamination film portion, and the groove is recessed from the surface of the circumferential lamination film portion, and
wherein the circumferential main body portion is not recessed in conformity with the groove.

2. The gasket according to claim 1, wherein the groove has a width of not less than 1 μm and not greater than 100 μm.

3. The gasket according to claim 1, wherein the groove includes at least one annular groove extending circumferentially in the surface of the circumferential lamination film portion.

4. The gasket according to claim 1, wherein the lamination film has a thickness of not less than 20 μm and not greater than 50 μm.

5. The gasket according to claim 1, wherein the groove has projections each having a thickness slightly greater than the original thickness of the circumferential lamination film portion along with outer edges of the groove.

6. The gasket according to claim 1, wherein a radial depth of the groove is less than a radial depth of the circumferential lamination film portion, and the groove is radially spaced apart from the surface of the circumferential main body portion by a portion of the circumferential lamination film portion.

7. The gasket according to claim 1, wherein the groove has a depth of not less than 1 μm and not greater than 50 μm.

8. The gasket according to claim 7, wherein the depth of the groove is not less than 5 μm and not greater than 15 μm.

9. The gasket according to claim 1, wherein the lamination film has a smaller thickness in the portion thereof formed with the groove than in the other portion thereof not formed with the groove.

10. The gasket according to claim 9, wherein the groove has a width of not less than 1 μm and not greater than 100 μm.

11. The gasket according to claim 9, wherein the groove has a depth of not less than 1 μm and not greater than 50 μm.

12. The gasket according to claim 11, wherein the depth of the groove is not less than 5 μm and not greater than 15 μm.

13. A medical syringe comprising:
a tubular syringe body;
a plunger combined with the syringe body and reciprocally movable in the syringe body; and
the gasket according to claim 1, the gasket being attached to a distal end of the plunger.

14. The medical syringe according to claim 13, which is a prefilled syringe in which the syringe body is prefilled with a liquid drug.

15. A method for producing the gasket according to claim 1, the method comprising the steps of: preparing a gasket molding mold; molding the gasket having the circumferential surface portion in the mold with the gasket being laminated with the lamination film; and demolding the gasket from the mold, and forming the groove only the lamination film circumferentially of the circumferential surface portion of the gasket.

16. The gasket production method according to claim 15, wherein the gasket molding step includes the step of placing an unvulcanized rubber in superposition on an inner surface of the lamination film in the mold, and vulcanization-molding the rubber.

17. The gasket production method according to claim 16, wherein the gasket molding step includes the step of roughening the inner surface of the lamination film before superposing the rubber on the inner surface of the lamination film.

18. The gasket production method according to claim 15, wherein the groove forming step includes the step of cutting a surface of the lamination film.

19. The gasket production method according to claim 18, wherein the groove forming step includes the step of laser-processing the lamination film.

* * * * *